(12) United States Patent
Dawes et al.

(10) Patent No.: US 8,815,763 B2
(45) Date of Patent: Aug. 26, 2014

(54) METHOD OF MANUFACTURING A TRANSITION METAL CATALYZED ZEOLITE BODY

(75) Inventors: Steven Bruce Dawes, Corning, NY (US); Steven Bolaji Ogunwumi, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 624 days.

(21) Appl. No.: 13/116,087

(22) Filed: May 26, 2011

(65) Prior Publication Data

US 2011/0294655 A1 Dec. 1, 2011

Related U.S. Application Data

(60) Provisional application No. 61/349,495, filed on May 28, 2010.

(51) Int. Cl.
| | | |
|---|---|---|
| *B01J 29/04* | (2006.01) | |
| *B01J 29/064* | (2006.01) | |
| *B01J 29/072* | (2006.01) | |
| *B01J 29/18* | (2006.01) | |
| *B01J 29/24* | (2006.01) | |
| *B01J 29/40* | (2006.01) | |
| *B01J 29/46* | (2006.01) | |
| *B01J 29/65* | (2006.01) | |
| *B01J 29/68* | (2006.01) | |
| *B01J 37/02* | (2006.01) | |
| *B01J 29/72* | (2006.01) | |
| *B01J 29/85* | (2006.01) | |
| *B01J 29/06* | (2006.01) | |
| *B01J 37/00* | (2006.01) | |
| B01J 37/08 | (2006.01) | |
| B01J 23/745 | (2006.01) | |

(52) U.S. Cl.
CPC ............ *B01J 29/072* (2013.01); *B01J 37/0205* (2013.01); *B10J 37/10* (2013.01); *B01J 29/46* (2013.01); *B01J 37/08* (2013.01); *B01J 2229/42* (2013.01); *B01J 29/723* (2013.01); *B01J 37/0207* (2013.01); *B01J 29/7215* (2013.01); *B01J 29/85* (2013.01); *B01J 29/68* (2013.01); *B01J 23/745* (2013.01); *B01J 29/061* (2013.01); *B01J 29/24* (2013.01); *B01J 37/0009* (2013.01)
USPC ................... 502/60; 502/74; 502/77; 502/78

(58) Field of Classification Search
None
See application file for complete search history.

(56) References Cited

U.S. PATENT DOCUMENTS 4,356,338 A * 10/1982 Young .......................... 585/407
4,381,253 A   4/1983 Shipley (Continued)

FOREIGN PATENT DOCUMENTS

JP    63248441 A  * 10/1988
WO   2009/073099    6/2009

OTHER PUBLICATIONS

JP 63248441, Mizuta et al, Oct. 1988, English Abstract.*

(Continued)

*Primary Examiner* — Melvin C Mayes
*Assistant Examiner* — Colin W Slifka
(74) *Attorney, Agent, or Firm* — Charles A. Greene; Joseph M. Homa

(57) ABSTRACT

A method of manufacturing a catalyst body which includes: soaking at least part of a fired zeolite-based body in a transition metal oxide solution; removing the body from the transition metal oxide solution; exposing the body to a humidified atmosphere at one or more temperatures above 20° C.; then drying the body; and calcining the body.

19 Claims, 1 Drawing Sheet

(56) References Cited

U.S. PATENT DOCUMENTS

| | | | |
|---|---|---|---|
| 5,387,564 A * | 2/1995 | Takeuchi et al. | 502/62 |
| 5,587,137 A | 12/1996 | Swaroop et al. | |
| 5,603,216 A | 2/1997 | Guile et al. | |
| 5,716,899 A | 2/1998 | Guile et al. | |
| 6,780,805 B2 | 8/2004 | Faber et al. | |
| 6,919,047 B1 | 7/2005 | He et al. | |
| 2002/0081255 A1 * | 6/2002 | Cutler et al. | 423/213.5 |
| 2003/0073567 A1 * | 4/2003 | Stamires et al. | 502/84 |
| 2008/0287283 A1 * | 11/2008 | Tepesch et al. | 502/62 |

OTHER PUBLICATIONS

JP 63-248441 A, Mizuta et al, Oct. 14, 1988, English Translation from STIC.*

* cited by examiner

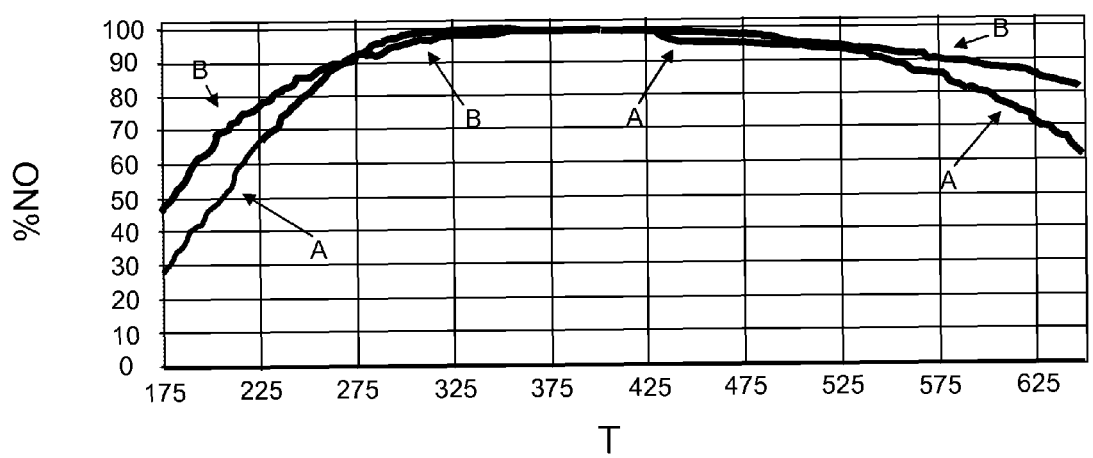

METHOD OF MANUFACTURING A TRANSITION METAL CATALYZED ZEOLITE BODY

CROSS REFERENCE TO RELATED APPLICATION

This application claims the benefit of priority under 35 U.S.C. §119 to U.S. Provisional Application No. 61/349,495, filed on May 28, 2010, the content of which is relied upon and incorporated herein by reference in its entirety.

FIELD

The present disclosure relates generally to methods of manufacturing catalyst bodies, such as zeolite-based bodies, such as extruded zeolite honeycomb bodies for use in engine exhaust systems.

BACKGROUND

Various methods and devices are known for reducing emissions of engine exhaust, including catalyst supports, substrates, and filters. The selective catalytic reduction (SCR) of nitrogen oxide is a process that is envisioned as part of an emissions control strategy needed to meet ever tightening legislated standards for lean exhaust systems. An example is a diesel exhaust systems which uses ammonia from urea for the selective catalytic reduction of NOx. Catalyst washcoating on honeycombs substrates and filters remains the incumbent process for the fabrication of these emissions control components.

SUMMARY

The present disclosure relates to methods of manufacturing catalyst bodies, such as extruded honeycomb catalyst bodies, such as for use in engine exhaust systems.

In one aspect, a method of manufacturing a catalyst body is disclosed herein, the method comprising: soaking at least part of a fired zeolite-based body in a transition metal oxide solution; then, removing the body from the transition metal oxide solution; then, exposing the body to a humidified atmosphere at one or more temperatures above 20° C.; then drying the body; then calcining the body. A zeolite-based body comprises zeolite, and has a primary phase of zeolite. In some embodiments, the zeolite-based body comprises a honeycomb structure. In some embodiments, the zeolite-based body comprises a foam structure, e.g. zeolite foam.

In some embodiments, the extruded honeycomb catalyst bodies of the present disclosure provide a operating temperature window exhibiting greater than 75% reduction of Nitric Oxide ("NO") gas in which the temperature of the NO gas is at least as low as 250° C. and at least as high as 600° C.

Additional features and advantages of the present disclosure will be set forth in the detailed description which follows, and will be readily apparent to those skilled in the art from that description or recognized by practicing the subject matter as described herein, including the detailed description which follows, the claims, as well as the appended drawings.

It is to be understood that both the foregoing general description and the following detailed description are intended to provide an overview or framework for understanding the nature and character of the inventions as claimed. The accompanying drawings and FIGURE are included to provide a further understanding of the disclosure, and are incorporated into and constitute a part of the specification.

The FIGURE illustrate various embodiments and aspects of the disclosure, and together with the description serve to explain the principles and operations of the claimed invention.

BRIEF DESCRIPTION OF THE DRAWINGS

FIGURE is a graphic illustration comparing $NO_x$ gas conversion ("% NO") vs. inlet temperature in ° C. ("T") for extruded zeolite Examples A and B as disclosed herein.

DETAILED DESCRIPTION

Reference will now be made in detail to the embodiments of the disclosure, examples and aspects of which are illustrated in the accompanying FIGURE.

In one aspect, a method of manufacturing a catalyst body is disclosed herein, the method comprising: soaking at least part of a fired zeolite body in a transition metal oxide solution; then, removing the body from the transition metal oxide solution; then, exposing the body to a humidified atmosphere at one or more temperatures above 20° C.; then drying the body; then calcining the body. In some embodiments, the catalyst body comprises between 0.5 and 5 wt % transition metal oxide after the calcining. In some embodiments, prior to the soaking step, the fired zeolite body is formed by extrusion and firing according to known methods. In some embodiments, wherein the transition metal oxide solution comprises iron, copper, or a combination thereof. In some embodiments, the transition metal oxide solution is an iron-containing solution. In some embodiments, the transition metal oxide solution is an iron gluconate solution. In some embodiments, substantially the entire fired zeolite body is immersed in the transition metal oxide solution.

In some embodiments, the drying of the body comprises exposing the body to an environment having a temperature of at least 100° C. In some embodiments, the drying of the body comprises exposing the body to an environment having a temperature which is increased at 5° C./minute to 100° C. and held at about 100° C. for about 1 hour. In some embodiments, the drying of the body comprises exposing the body to an environment having a temperature which is increased at 5° C./minute to 100° C. and held at one or more temperatures and for a time sufficient to achieve a water loading of less than 5 wt % in the body after the drying step.

In some embodiments, the exposing of the body to the humidified atmosphere comprises placing the body in a closed container and heating the atmosphere within the container to 80° C. for at least 20 hours. In some embodiments, the exposing of the body to the humidified atmosphere comprises placing the body in a closed container and heating the atmosphere within the container to at least 50° C. for at least 10 hours.

In some embodiments, the calcining comprises exposing the body to an environment of greater than 500° C. for more than 1 hour. In some embodiments, the calcining comprises exposing the body to an environment of greater than 500° C. for more than 2 hours. In some embodiments, the calcining comprises exposing the body to an environment of greater than 500° C. for more than 2 hours.

In some embodiments, the fired zeolite body comprises one or more of the group consisting of silicoaluminophosphate having silicon to alumina ratio less than 50, zeolite beta, ZSM-5, mordenite, chabazite, and ferrierite.

In some embodiments, the fired zeolite body comprises a honeycomb structure.

The method may further comprise hydrating the fired zeolite body prior to the soaking. For example, the fired zeolite body is hydrated by exposing the body to a heated, high humidity environment. In some embodiments, the fired zeolite body is hydrated by exposing the body to an environment having a temperature of at least 50° C. and 100% relative humidity for at least 3 hours. In some embodiments, the fired zeolite body is hydrated by exposing the body to an environment having a temperature of at least 80° C. and 100% relative humidity for at least 4 hours. In some embodiments, the fired zeolite body prior to the soaking has a total pore volume, and after the hydrating, a water mass of 5 to 10% of the total pore volume is added to the body.

The method may further comprise, after the removing of the body, blowing the body with a gas stream. The gas stream blown at the body can remove any excess portion of transition metal oxide solution from the body. Preferably, the gas stream blown at the body removes a portion of transition metal oxide solution from an outside surface of the body; we have found that excess transition metal oxide on the outer surface of the body can decrease catalytic performance, e.g. a decrease in NO conversion efficiency at higher temperatures.

In some embodiments, after the calcining of the body, the catalyst body is inserted into a metal container for use in an engine exhaust system without being subjected to a washcoating process, i.e. without a washcoat being applied to the catalyst body, i.e. an unwashcoated catalyst body. In other embodiments, after the calcining of the body, the catalyst body is subjected to a washcoating process, and the washcoated body is inserted into a metal container for use in an engine exhaust system.

In some embodiments, the catalyst body is especially suited in applications for treating diesel and lean burning engine exhaust containing $NO_x$, HC and ammonia gas.

In some embodiments, the catalyst body manufactured as disclosed herein can be used in an engine exhaust system, for example in the selective catalytic reduction (SCR) of nitrogen oxide with ammonia, such as for diesel engines. In some embodiments, the catalyst body can accommodate the SCR reaction even when reaction conditions change over a normal duty cycle for the engine, for example with reaction temperature varying from 200° C. to over 500° C., and even with temperature excursions to greater than 600° C.

The selective reduction process is known as the SCR process (Selective Catalytic Reduction). The SCR process uses the catalytic reduction of nitrogen oxides with ammonia in the presence of atmospheric oxygen with the formation predominantly of nitrogen and steam, such as given by one of the following stoichiometries:

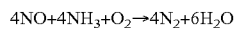
$$4NO+4NH_3+O_2 \rightarrow 4N_2+6H_2O$$

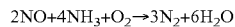
$$2NO+4NH_3+O_2 \rightarrow 3N_2+6H_2O$$

$$NO+NO_2+2NH_3 \rightarrow 2N_2+3H_2O$$

In some preferred embodiments, these nitrogen reactions proceed rapidly, and as close as possible to completion, over a broad operating temperature window, with minimal unreacted ammonia passing into the vehicle exhaust, i.e. with minimal ammonia slip.

At the same time, competing reactions are advantageously not catalyzed. A particularly problematic competing reaction is the oxidation of ammonia, which can occur at higher temperatures, as follows:

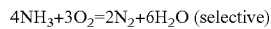
$$4NH_3+3O_2=2N_2+6H_2O \text{ (selective)}$$

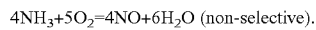
$$4NH_3+5O_2=4NO+6H_2O \text{ (non-selective)}.$$

Ammonia oxidation can at a minimum disturb the SCR stoichiometry, and can even increase NO content of the exhaust stream. For conversion of $NO_x$ to $N_2$ at desired levels, a catalyst should be advantageously active; for example at temperatures as lows as 200 C and at a space velocity of at least 20,000/hr, a 500 ppm NO inlet could have 30% or more conversion; under similar flow conditions, the catalyst could convert greater than 80% of the NO at 550 C.

EXAMPLES

The disclosure may be further understood by reference to the following examples, which are intended to be merely illustrative of the compositions and methods for carrying out the invention.

Iron gluconate solutions (stock solution) were prepared by mixing iron gluconate in a solvent comprising 150 cc water and 2.4 cc ammonium-hydroxide. The formulation of iron gluconate was determined for a given target catalyst composition by determining the pore volume of an extrudate of known zeolite mass. For example an extrudate containing 3 grams of zeolite with 1 cc of pore volume can be catalyzed with a target $Fe_2O_3$ level of 1 wt % relative to zeolite by formulating the precursor of 0.03 gram of $Fe_2O_3$ (0.18 grams ferrous gluconate) in 1 cc solution. 150 cc of stock solution would require 27 grams of iron gluconate (FeG).

Example A

A zeolite-based body was formed by mixing zeolite beta (Si:Al of 25) and silica binder, and the mixture was extruded into a honeycomb structure having 400 cells per square inch, the cells being bounded by walls 6 mils thick, and the honeycomb structure was fired to yield the body with 72 wt % zeolite beta and 28 wt % silica with a pore volume of 0.86 cc/g. The extruded zeolite containing body was cut to a nominal dimension of 1" diameter by 1" long. The sample was warmed to 100° C. to vaporize water and weighed. The pore volume of the sample was estimated by soaking the body in water and re-weighing after lightly blowing-out excess water from the channels. A target stock solution was prepared based on the zeolite weight and pore volume. The catalyzing was done in three steps: The sample was soaked by immersion into the stock solution for at least one hour, and then was removed and excess solution was lightly blown out of the channels. It was observed that some ion exchange occurs rapidly during the soaking of the sample, so as the pore volume is replenished with ions from the stock solution, the total uptake of iron exceeds the pore volume total alone, which can lead to a slight acceptable excess over the target loading. The sample was then dried and aged by placing the wet sample into a closed tube and heating at 80 C for one day, before opening the tube and warming to 100° C. until dry. Following the drying step the sample was optionally rinsed to remove excess iron gluconate from the external surface of the material. The rinse process entailed placing the sample in distilled water for 5 minutes, and then blowing out excess water. After catalyzing the sample was placed in an oven at room temperature, and was ramped to 100 C at 5° C./minute and dried for 1 hour, then was calcined in a furnace by ramping at 10° C./minute to 550° C. for 3 hours. Immersion of dry zeolite containing extrudates into water can lead to rapid expansion of the body, and cracking if the body strength is too low. To avoid cracking of extruded parts on immersion into a stock solution or rinse step, the extrudates were pre-conditioned by a slow hydration step. The parts were placed onto a platform above water in a closed container and then heated to 80° C. for 4 hours to effect an 80° C./100% RH environment. After such a treatment the samples picked up water mass equal to about 10% of the total pore volume.

Example B

A zeolite-based body was formed by mixing zeolite beta (Si:Al of 25) and silica binder and alumina filler, and the mixture was extruded into a honeycomb structure having 400 cells per square inch, the cells being bounded by walls 6 mils thick, and the honeycomb structure was fired to yield the body with 49 wt % zeolite beta and 17 wt % silica and 33 wt % alumina with a pore volume of 0.6 cc/g. The extruded zeolite containing body was otherwise catalyzed in the same manner as Example A.

The samples were tested for SCR activity by monitoring the NO reduction by ammonia as a function of temperature in a flowing reactant stream containing 500 ppm NO, 500 ppm $NH_3$, 5% $H_2O$, 10% $O_2$ with the remainder nitrogen. The total flow rate was set at 20,000 times the sample volume per hour.

FIGURE is a graphic illustration comparing $NO_x$ gas conversion for Examples A and B.

The NO conversion results from FIGURE were obtained using a linch lab bench reactor at 20000 space velocity. The inlet gas composition was 500 ppm NO, 500 ppm $NH_3$, 10% $O_2$, 5% $H_2O$, and balance $N_2$. The gases (NO and $NH_3$) were detected by FTIR detector. As shown in FIGURE, the NO conversion is plotted vs. inlet gas temperature (° C.); Examples A and B each achieved greater than 50% NO conversion at temperatures between 225 and 625° C., and greater than 70% NO conversion at inlet temperatures between 250° C. and 600° C. Examples A and B also both provide greater than 80% NO conversion at inlet temperatures between 275° C. and 575° C.

The catalyst bodies can be produced by mixing batch materials, blending the mixture, forming a green body, and subsequently sintering or firing the green body to a hard porous structure. A batch mixture suitable for extrusion can be prepared by mixing the components described above with a suitable liquid vehicle. The vehicle may comprise water and extrusion aids necessary to give the batch plastic formability and sufficient green strength after forming to resist breakage prior to firing. Various lubricants, binders, surfactants, pore-formers, and viscosity modifiers can be added to the batch during the mixing step to provide viscosity control, plasticity, and strength prior to firing, and porosity to the fired structure.

Embodiments of the extruded catalyst-based honeycomb bodies of the present disclosure can be particularly suited for use as flow through substrates or as exhaust filters such as in diesel exhaust and lean burn exhaust systems. The honeycomb bodies of the present disclosure preferably exhibit high surface area and low thermal expansion, and in some embodiments reduce or eliminate the need for excessive high surface area washcoating.

In some of embodiments, the honeycomb body is a flow through substrate. In other embodiments, the honeycomb body is a wall flow filter, such as a particulate filter, for example a diesel particulate filter. In filter embodiments, some of the cells may be plugged so as to seal the respective cell channels in the so-formed catalyst-based honeycomb body. For example, in some embodiments a portion of the inlet end cell channels are plugged and a portion of the outlet end cell channels are plugged but not corresponding to those at the inlet end, such that each cell is plugged at one end only. Plugging at the ends of the cell channels is preferably accomplished with plugs having a depth of about 5 mm to 20 mm. In some embodiments, the arrangement is to have every other cell channel on a given end plugged in a checkered pattern.

In some embodiments, the present disclosure provides a method for "post catalyzing" an extruded zeolite monolith (such as a honeycomb structure), i.e. catalyzing an extruded zeolite monolith after extrusion (post-extrusion) that could be utilized as a flow through NOx substrate or an integrated NOx and soot particulate reduction filter for engine exhaust treatment. The method can provide a catalyzed zeolite body which has the ability to perform as well as, or even better than, a pre-exchanged zeolite body that is extruded or an extruded body incorporating the catalyst during the batch formulation prior to extrusion (i.e. "co-catalyzing"). The method disclosed herein helps to reduce the challenges and limitations of processing using the co-catalyzing approach. The method disclosed herein may also help to allow for variation in the resulting catalysts composition and catalyst concentration after the body is formed. The method disclosed herein can also help to offer flexibility in allowing the catalyst to be distributed in a desired portion or section of the honeycomb body.

The method disclosed herein can help improve the SCR catalyst performance of a post catalyzed extruded zeolite honeycomb structure. The method can, in some embodiments, eliminate the need for a high surface area washcoat before incorporation of the active metal on the surface by an exchange or impregnation of the soluble active metal from a precursor solution onto the extruded high surface zeolite area body, which could eliminate the challenges of dealing with washcoat slurries which sometimes results in adhesion issues. The method disclosed herein can thus provide a back-pressure advantage over having a washcoat, while allowing the flexibility of zone catalyst coating and increased catalyst concentration for good performance and durability. In other embodiments, additional washcoating of high surface area material could be utilized for added catalytic functionality.

It will be apparent to those skilled in the art that various modifications and variations can be made to the present disclosure without departing from the spirit and scope of the invention. Thus it is intended that the present invention cover the modifications and variations of this disclosure provided they come within the scope of the appended claims and their equivalents.

What is claimed:

1. A method of manufacturing a catalyst body, the method comprising:
   hydrating a fired zeolite body having a total pore volume by exposing the fired zeolite body to an environment having a temperature of at least 50° C. and a relative humidity of 100%, including carrying out said hydrating until a water mass of 5% to 10% of the total pore volume is added to the fired zeolite body; then,
   soaking at least part of the hydrated fired zeolite body in a transition metal oxide solution; then,
   removing the body from the transition metal oxide solution; then,
   exposing the body to a humidified atmosphere at one or more temperatures above 20° C.; then
   drying the body; then
   calcining the body.

2. The method of claim 1 wherein the catalyst body comprises between 0.5 and 5 wt % transition metal oxide after the calcining.

3. The method of claim 1 wherein, prior to the soaking step, the fired zeolite body is formed by extrusion and firing.

4. The method of claim 1 wherein the transition metal oxide solution comprises iron, copper, or a combination thereof.

5. The method of claim 1 wherein the transition metal oxide solution is an iron-containing solution.

6. The method of claim 1 wherein the transition metal oxide solution is an iron gluconate solution.

7. The method of claim 1 wherein substantially the entire fired zeolite body is immersed in the transition metal oxide solution.

8. The method of claim 1 wherein the hydrating is performed for at least 3 hours.

9. The method of claim 1 wherein the hydrating is performed for at least 4 hours.

10. The method of claim 1 further comprising, after the removing of the body, blowing the body with a gas stream.

11. The method of claim 10 wherein the gas stream blown at the body removes a portion of transition metal oxide solution from the body.

12. The method of claim 10 wherein the gas stream blown at the body removes a portion of transition metal oxide solution from an outside surface of the body.

13. The method of claim 1 wherein the drying of the body comprises exposing the body to an environment having a temperature of at least 100° C.

14. The method of claim 1 wherein the drying of the body comprises exposing the body to an environment having a temperature which is increased at 5° C./minute to 100° C. and held at one or more temperatures and for a time sufficient to achieve a water loading of less than 5 wt % in the body.

15. The method of claim 1 wherein the exposing of the body to the humidified atmosphere comprises placing the body in a closed container and heating the atmosphere within the container to at least 50° C. for at least 10 hours.

16. The method of claim 1 wherein the calcining comprises exposing the body to an environment of greater than 500° C. for more than 1 hour.

17. The method of claim 1 wherein the calcining comprises exposing the body to an environment of greater than 500° C. for more than 2 hours.

18. The method of claim 1 wherein the fired zeolite body comprises one or more of the group consisting of: silicoaluminophosphate having silicon to alumina ratio less than 50, zeolite beta, ZSM-5, mordenite, chabazite, and ferrierite.

19. The method of claim 1 wherein the fired zeolite body comprises a honeycomb structure.

* * * * *